United States Patent
Mais et al.

(10) Patent No.: US 6,706,934 B2
(45) Date of Patent: Mar. 16, 2004

(54) METHOD FOR PRODUCING 2,3,4,5-TETRACHLOROBENZOTRIFLUORIDE

(75) Inventors: Franz-Josef Mais, Düsseldorf (DE); Helmut Lahr, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/239,981

(22) PCT Filed: Mar. 19, 2001

(86) PCT No.: PCT/EP01/03112
§ 371 (c)(1),
(2), (4) Date: Sep. 26, 2002

(87) PCT Pub. No.: WO01/74746
PCT Pub. Date: Oct. 11, 2001

(65) Prior Publication Data
US 2003/0078459 A1 Apr. 24, 2003

(30) Foreign Application Priority Data
Mar. 31, 2000 (DE) .......................... 100 16 192

(51) Int. Cl.⁷ .................. C07C 22/00; C07C 25/13; C07C 17/00; C07C 25/00
(52) U.S. Cl. .................. 570/144; 570/127; 570/208; 570/210
(58) Field of Search ................ 570/127, 144, 570/208, 210

(56) References Cited

U.S. PATENT DOCUMENTS

| 4,401,623 A | 8/1983 | Giacobbe et al. .............. 422/1 |
| 5,599,980 A | 2/1997 | Marhold et al. ............ 562/840 |
| 5,750,811 A | 5/1998 | Buchanan et al. .......... 570/208 |

OTHER PUBLICATIONS

*Ushakov A A et al: "Features of the high chlorination of 4–chloro– and 2,4–dichlorotrifluoromethyl–Benzenes" Journal of Organic Chemistry of the USSR. (Zhurnal Organischeskoi Khimii), Bd. 20, Nr. 10, 1984, Seiten 1993–1996, XP002171256 Consultants Bureau. New York., US in der Anmeldung erwähnt Tabelle 1.

Zhurnal Organicheskoi Khimii, vol. 20, (month unavailable) 1984, pp. 2187–2191.

*Primary Examiner*—Porfirio Nazario-Gonzalez
*Assistant Examiner*—Elvis O. Price
(74) *Attorney, Agent, or Firm*—Godfried R. Akorli; Diderico van Eyl

(57) ABSTRACT

Disclosed herein is a method for producing 2,3,4,5-tetrachlorobenzotrifluoride comprising chlorinating 4-chlorobenzotrifluoride with elemental chlorine, in the presence of from 0.1 to 2% by weight of iron(III) chloride and 0.05 to 0.75% by weight of aluminum(III) chloride, in each case based on 4-chlorobenzotrifluoride, where the weight ratio of iron(III) chloride to aluminum(III) chloride is 10:1 to 1:1.

6 Claims, No Drawings

METHOD FOR PRODUCING 2,3,4,5-TETRACHLOROBENZOTRIFLUORIDE

This is a 371 PCT Application of serial number PCT/EP01/03112 filed Mar. 19, 2001.

The present invention relates to an improved method for producing 2,3,4,5-tetrachlorobenzotrifluoride from 4-chlorobenzotrifluoride.

2,3,4,5-Tetrachlorobenzotrifluoride is an intermediate for the preparation of highly effective antibacterial quinolonecarboxylic acid derivatives (see e.g. U.S. Pat. No. 5,599,980).

A kinetic investigation of the chlorination of 4-chlorobenzotrifluoride with chlorine in the presence of iron is reported in Zh. Org. Khimii 20, 2187–2191 (1984). According to this, the tetrachlorobenzotrifluoride formed is virtually only the 2,3,4,5-isomer. A preparative production of 2,3,4,5-tetrachlorobenzotrifluoride is not described therein. In the experimental section of this literature source, a chlorination rate of 0.1 g/mol.h is given. For the production of tetrachlorobenzotrifluoride, that would mean a chlorination time of more than 2000 hours, which is much too long for a preparative method.

A production method for 2,3,4,5-tetrachlorobenzotrifluoride in which 4-chlorobenzotrifluoride is reacted with chlorine in the presence of iron sulfide as catalyst is known from U.S. Pat. No. 5,599,980. Here, the desired product is obtained in a yield of only 56.8% of theory, which is very unsatisfactory.

A disadvantage of all of the methods known hitherto is the elimination of hydrogen fluoride, which proceeds as a secondary reaction. This leads to corrosion problems and impairs the quality of the hydrochloric acid formed. In the production of 3,4-dichlorobenzotrifluoride, an intermediate in the production of 2,3,4,5-tetrachlorobenzotrifluoride from 4-chlorobenzotrifluoride, this problem was solved by adding calcium chloride to the iron(III) chloride catalyst (see U.S. Pat. No. 4,401,623). However, such a process cannot be transferred to the production of 2,3,4,5-tetrachlorobenzotrifluoride since the absorption of hydrogen fluoride by calcium chloride is reversible (see loc. cit., column 3, lines 14 ff). For the production of 2,3,4,5-tetrachlorobenzotrifluoride, higher temperatures are required than for the production of 3,4-dichlorobenzotrifluoride, which favors the desorption of hydrogen fluoride. According to U.S. Pat. No. 4,401,623, at the minimum temperature of e.g. 80° C. required for the production of 2,3,4,5-tetrachlorobenzotrifluoride, the corrosion rate is already higher by a factor of 5 than at the temperature of 60° C. which is otherwise used therein (see in particular column 4, Table II).

There is therefore still a need for a method for producing 2,3,4,5-tetrachlorobenzotrifluoride in which shorter reaction times, better yields and reduced contents of hydrogen fluoride in the reaction mixture and in the offgas and thus an improvement in the corrosion rate are possible.

We have now found a method for producing 2,3,4,5-tetrachlorobenzotrifluoride by chlorinating 4-chlorobenzotrifluoride with elemental chlorine, which is characterized in that the chlorination is carried out in the presence of from 0.1 to 2% by weight of iron(III) chloride and 0.05 to 0.75% by weight of aluminum(III) chloride, in each case based on 4-chlorobenzotrifluoride, where the weight ratio of iron(III) chloride to aluminum(III) chloride is 10:1 to 1:1.

The method according to the invention can be carried out, for example, at temperatures in the range 80 to 150° C. Preference is given to working at 100 to 130° C.

The pressure is not critical for the method according to the invention. It is possible to work below atmospheric pressure, above atmospheric pressure or at atmospheric pressure. Preference is given to working at atmospheric pressure or at pressures up to 1.5 bar.

The method according to the invention can be carried out with or without solvent additions. Suitable solvents are, in particular, halogenated hydrocarbons. Preference is given to working without solvent additions, i.e. without a diluent.

The reagents and auxiliaries required for the method according to the invention can be used in standard commercial grades. The water content of the 4-chlorobenzotrifluoride is preferably less than 100 ppm, and the water content of the chlorine is preferably less than 50 ppm. Iron(III) chloride and aluminum(III) chloride can be used with the low water contents with which they are available commercially.

Based on 4-chlorobenzotrifluoride, preference is given to using 0.25 to 1% by weight of iron(III) chloride and 0.1 to 0.3% by weight of aluminum(III) chloride, where the weight ratio of iron(III) chloride to aluminum(III) chloride is 5 to 1.5:1.

The method according to the invention can be carried out in various ways, e.g. discontinuously, continuously or semi-continuously in pulses. As an example, in the discontinuous procedure it is possible, for example, to initially introduce 4-chlorobenzotrifluoride, to add iron(III) chloride and aluminum(III) chloride, to heat the mixture, with stirring, to the reaction temperature and to gas with chlorine until the desired conversion is reached. The gassing with chlorine can be stopped, for example, when the content of 2,3,4,5-tetrachlorobenzotrifluoride in the reaction mixture is 70 to 80% by weight. The desired product can then be isolated from the reaction mixture, for example by distillation. Chlorobenzotrifluorides with a lower degree of chlorination are produced here as forerunnings and can be returned to the chlorination.

The method according to the invention permits the production of 2,3,4,5-tetrachlorobenzotrifluoride in shorter reaction times and with better yields. This is surprising since iron(III) chloride and aluminum(III) chloride are often equivalent Lewis acid catalysts. Here, however, they surprisingly interact in a synergistic way.

It is also surprising that the use according to the invention of aluminum(III) chloride leads to greatly reduced contents of hydrogen fluoride in the reaction mixture and in the offgas. It is known from U.S. Pat. No. 5,599,980 (see column 7, line 64 to column 8, line 9) that it is possible to produce tetrafluorobenzotrichloride from tetrafluorobenzotrifluoride at temperatures as low as 40° C. using aluminum(III) chloride. On the basis of this prior art, it is thus expected that, in the presence of aluminum(III) chloride, the contents of hydrogen fluoride in the reaction mixture and in the offgas would be increased, and that corrosion problems caused thereby would be greater. Surprisingly, in the method according to the invention, only low contents of hydrogen fluoride arise in the reaction mixture and in the offgas.

Finally, in the method according to the invention, it is possible to isolate from the offgas a hydrochloric acid which can be used generally, whereas in the case of increased contents of hydrogen fluoride, it is only possible to obtain from the offgas a hydrogen fluoride-containing hydrochloric acid which, due to its high corrosion potential, can only be used for specific purposes.

EXAMPLES

Example 1

100 parts by weight of 4-chlorobenzotrifluoride were introduced into a stirred vessel. To this were added 0.5 parts by weight of iron(III) chloride and 0.167 parts by weight of aluminum(III) chloride. The mixture was heated to 110° C. with stirring and 166 parts by weight of chlorine were introduced, with stirring, over the course of 117 hours. After nitrogen had been blown through for 3 hours, 157 parts by weight of a reaction mixture of the following gas chromatographically ascertained composition were obtained: 0.8% by weight of dichlorobenzotrifluorides, 13.5% by weight of trichlorobenzotrifluorides, 74.1% by weight of 2,3,4,5-tetrachlorobenzotrifluoride and 8.0% by weight of pentachlorobenzotrifluoride. This corresponds to a yield of 2,3,4,5-tetrachlorobenzotrifluoride of 74.0% of theory. The offgas was analyzed for the content of hydrogen fluoride. It was less than 5 ppm between the 80th hour and the end of the chlorination. The dichloro- and trichlorobenzotrifluorides, which are produced with a yield of 1.1 or 15.3% of theory, respectively, can be recycled after being separated off by distillation.

Example 2
For Comparison Procedure Only with Iron(III) Chloride as Catalyst 100 parts by weight of 4-chlorobenzotrifluoride were introduced into a stirred vessel. To this were added 0.5 parts by weight of iron(III) chloride. The mixture was heated to 110° C. with stirring, and 166 parts by weight of chlorine were introduced such that a product composition was produced which was as similar as possible to that of Example 1, which required 126 hours. After nitrogen had been blown through for 3 hours, 150 parts by weight of a reaction mixture of the following gas chromatographically ascertained composition were obtained: 1.2% by weight of dichlorobenzotrifluorides, 13.8% by weight of trichlorobenzotrifluorides, 73.4% by weight of 2,3,4,5-tetrachlorobenzotrifluoride and 7.1% by weight of pentachlorobenzotrifluoride. This corresponds to a yield of 70.1% of theory. The offgas was analyzed for the content of hydrogen fluloride. It was between 40 and 50 ppm between the 80th hour and the end of the chlorination.

What is claimed is:

1. A method for producing 2,3,4,5-tetrachlorobenzotrifluoride comprising chlorinating 4-chlorobenzotrifluoride with elemental chlorine, in the presence of from 0.1 to 2% by weight of iron(III) chloride and 0.05 to 0.75% by weight of aluminum(III) chloride, in each case based on 4-chlorobenzotrifluoride, where the weight ratio of iron(III) chloride to aluminum(III) chloride is 10:1 to 1:1.

2. The method as claimed in claim 1, carried out at temperatures in the range 80 to 150° C.

3. The method as claimed in claim 1, carried out without solvent additions.

4. The method as claimed in claim 1, wherein the water content of the 4-chlorobenzotrifluoride used is less than 100 ppm and the water content of the chlorine used is less than 50 ppm.

5. The method as claimed in claim 1, wherein, based on 4-chlorobenzotrifluoride, 0.25 to 1% by weight of iron(III) chloride and 0.1 to 0.3% by weight of aluminum(III) chloride are used, and where the weight ratio of iron(III) chloride to aluminum(III) chloride is 5 to 1.5:1.

6. The method as claimed in claim 1, carried out discontinuously, continuously or semicontinuously in pulses.

* * * * *